United States Patent [19]
Kreider et al.

[11] Patent Number: 5,541,058
[45] Date of Patent: Jul. 30, 1996

[54] IN VITRO ASSAY SYSTEM FOR TESTING THE EFFECTIVENESS OF ANTI-PAPILLOMA VIRAL AGENTS

[76] Inventors: John W. Kreider, Box 297 R.D. 1, Palmyra, Pa. 17078; Michael G. Angell, 10577 Livingston St., Hamburg, Mich. 48139

[21] Appl. No.: 118,948

[22] Filed: Sep. 9, 1993

[51] Int. Cl.$^6$ .............................. C12Q 1/68; C12Q 1/70
[52] U.S. Cl. ............................................ 435/5; 435/6
[58] Field of Search ........................... 435/5, 6, 172.1, 435/240.2

[56] References Cited

PUBLICATIONS

Reilly et al. Cancer Cell 5, 1987, Cold Spring Harbor Lab. pp. 159–163.
Christian et al., Cancer Cell 5, 1987, Cold Spring Harbor Lab. pp. 165–169.
Angell et al., 1992, J. Vir. Methods, vol. 39, pp. 207–216.
Dollard et al., in Genes and Development, 1992, Cold Spring Harbor Lab., pp. 1131–1142.
Merta et al., 1990, Antiviral Research, vol. 13, pp. 209–218.
Watts et al., 1983, Virology, vol. 125, pp. 127–138.
Breidahl et al., 1990, Immunol. Cell Biol. vol. 68, pp. 119–126.
Christiansen et al., 1991, Virus Research, vol. 21, pp. 169–179.
Meyers et al., 1992, Science, vol. 257, pp. 971–973.
De Clercq et al., 1986, Nature, vol. 323, pp. 464–467.
Seto et al., J. Invest. Dermatol., 1991, vol. 97, pp. 327–333.
Taichman et al., 1984, J. Investig. Dermatol. vol. 83, pp. 2s–6s.
Kreider et al., 1981, Advanc. Cancer research, vol. 35, pp. 81–110.
Meyers et al., 1992, J. Virol. vol. 66, pp. 1655–1664.
Georges et al., 1985, J. Virol., vol. 55, pp. 246–250.
Georges et al., 1984, J. Virol. vol. 51, pp. 530–538.
Meyers et al., 1991, Virology, vol. 181, pp. 637–646.

*Primary Examiner*—Mindy Fleisher
*Assistant Examiner*—David Guzo

[57] ABSTRACT

An in vitro method for testing the effectiveness of antiviral agents is provided. The method allows for screening anti-papillomavirus drugs which can interfere with the early and maintenance stages of papillomavirus infection. The method comprises growing epithelial cells susceptible to infection with papillomavirus in a monolayer system and measuring the effectiveness of various agents present in the growing media to interfere with the growth of the virus. The method is free from interferences caused by the regional variability, since the cell cultures are evenly dispersed monolayers.

5 Claims, 15 Drawing Sheets

PMEG Toxicity on CRPV-Infected Sf1Ep Cells

- ○ – Diluent
- □ – 0.1 ug/ml
- △ – 1.0 ug/ml
- ▼ – 10.0 ug/ml

Cell number per sq mm vs. Treatment Duration (Days)

IN VITRO ASSAY SYSTEM FOR TESTING THE EFFECTIVENESS OF ANTI-PAPILLOMA VIRAL AGENTS

GOVERNMENT SPONSORSHIP

This invention was made with Government support under PHS Grant No. AI82687 awarded by the National Institutes of Health. The Government has certain rights in the invention.

FIELD OF INVENTION

This invention relates to a novel in vitro method of testing antiviral activity of various agents. More specifically, it describes a method of testing effectiveness of anti-papillomavirus agents which act early in the infection process. The method is useful in testing effectiveness of existing and potential antiviral drugs, in particular, future drugs directed to treatment of human papilloma virus infections.

BACKGROUND OF THE INVENTION

Testing of the antiviral effectiveness of the new and existing agents against human papillomavirus are still performed in the in vivo testing involving use of laboratory animals and human subjects. These studies are expensive, time consuming and altered by individual differences among subjects.

A demonstration of efficacy prior to in vivo animal model testing would limit the candidate in vivo agents to the ones with increasing potential for in vivo effectiveness. This is especially important for those newer, more speculative agents for which purer antiviral effects are lacking. In vitro demonstration of efficacy would support a decision for expensive testing in animal model systems. In vitro studies are also useful for exploring drug-virus interactions which are awkward or infeasible in whole animal systems. In vitro testing offers the following advantages: 1) preliminary data on efficacy; 2) rapid turn around time; 3) economy; 4) ability to precisely control environmental conditions; 5) elimination of pharmacokinetics and variability of whole animal systems; and 6) small amounts of drugs are required.

Unfortunately, there are no established systems for in vitro papillomavirus testing. There have been some recent, encouraging developments, elsewhere and in our laboratory. Broker's laboratop/has recently suggested that the xenograft system, which we originated, might be useful for antiviral testing (S. Dollard, et al., 1992, Gene Dev., 6:1131–1142).

In that one approach, fragments of HPV-11 infected human foreskin tissue is excised from the papillomatous cysts, growing beneath the renal capsule, and the fragments are placed onto a collagen gel "raft" culture. HPV-11 replication continues in the tissue fragment, as cells migrate laterally across the surface of the gel. We have explored the use of this system as a possible target for antiviral testing, and we have found that there is a high degree of regional variability in the extent of cell migration, tissue growth, and HPV-11 replication. We do not believe that this in vitro system is sufficiently consistent or precise to form a basis for tests. Further, since preliminary xenografts are required, the cost of the test includes their preliminary growth for three months, so some of the theoretical advantages of in vitro tests, economy and rapid turn-around are lacking.

Another in vitro system with potential was recently described by Laimins' group (Meyers, et al., 1992, Science, 257:971–973). In this system, human cervical cells, bearing HPV-31b episomal DNA are placed on collagen gel raft cultures and biosynthesis of complete virions occurs in the differentiating cells. It seems likely that this system may also be affected by regional variability.

Many of the disadvantages of the prior art methods of testing antiviral activity are overcome by the method of the present invention which precisely measures antiviral activity without the interferences of the regional variability, since the cell cultures are evenly dispersed monolayers.

SUMMARY OF THE INVENTION

In accordance with the present invention, a new in vitro method of testing of the antiviral activity of the potential agents in the initial stages of papillomavirus infection is presented.

In our laboratory, we have recently developed a monolayer cell culture system in which we have conducted antiviral testing. The monolayer is a uniform cell sheet with no regional variability. The system can use, alternatively, two rabbit epithelial cell lines: RK-13, derived from domestic rabbit kidney, and SF1Ep, derived from cottontail epidermis. The cells are planted in vitro, infected with cottontail rabbit papillomavirus CRPV virion, and this is soon followed by a wave of CRPV DNA replication and mRNA synthesis, probably ORFs E6 and E7. Under these conditions, the epithelial cells do not complete cytodifferentiation, a requisite for complete virion synthesis, so the papillomavirus infection is abortive, and the CRPV DNA is lost after 3–5 passages. However, only a few days post-infection is sufficient for antiviral testing.

Testing of the antiviral activity involves exposing cells to the various amount of the agent and measuring the effect on the level of CRPV transcription and cell proliferation/viability.

Our studies showed that CRPV infection of an established cottontail epidermal cell line (Sf1Ep) resulted in the production of CRPV-specific transcripts without concomitant morphological transformation (M. Angell, et al., J. Vir. Meth., 1992, 39:207–216). The most abundant transcripts corresponded in size to those of the E6 and E7 open reading frames (ORFs) which are also among the most abundant in domestic and cottontail rabbit papillomas. CRPV RNA production was both time and dose-dependent with RNA production diminishing with decreasing viral dose and increasing culture passage. Infected cultures contained episomal CRPV DNA which did not appreciably change in abundance with time but was significantly reduced with culture passage. All features of in vitro infection, especially RNA production, were inhibited by CRPV-neutralizing but not HPV-11-neutralizing monoclonal antibodies. Much of this inhibition could be attributed to a blockage of vital penetration as indicated by the reduction of CRPV DNA within virus-neutralized cultures. Our results indicated that although CRPV infection of SflEp cells was abortive, it serves as a useful model for analysis of early infection events.

Substituting the neutralizing antibody with an antiviral agent has proven to be a useful way of measuring the effectiveness of the antiviral agents and formed the basis for the novel method of testing the antiviral activity of unknown agents.

OBJECTS OF THE INVENTION

An object of this invention is to provide a novel method of in vitro testing of the antiviral activity of potential antiviral agents.

DETAILED DESCRIPTION OF THE INVENTION

Figure 1:
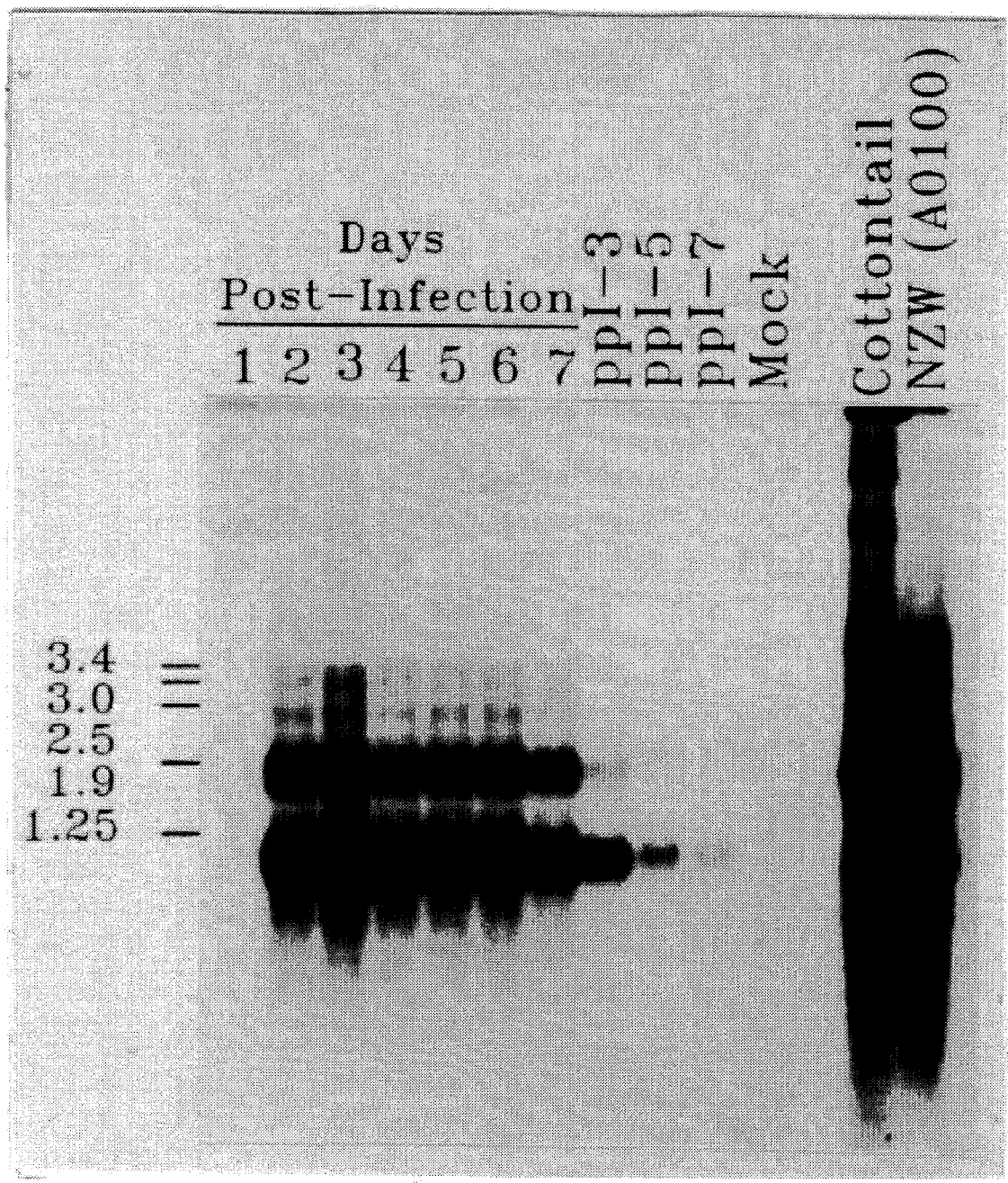
FIG. 1. Northern hybridization of CRPV-infected Sf1Ep cultures. Each sample represents 10 micrograms of total cellular RNA. Samples represent infected cultures days 1–7 after infection as well as cultures passaged (1:2 split every 3rd day) 3, 5 or 7 times after infection (ppl). Cottontail and NZW (A0100) represent RNA isolated from a CRPV-infected cottontail rabbit earskin papilloma cyst and New Zealand White (domestic) rabbit papilloma respectively. Mock indicates RNA isolated from mock infected Sf1Ep cells. Transcript sizes were based on the migration of RNA standard ladders.

The present invention describes the scientific basis as well as preferred way of performing the novel method of testing effectiveness of potential antiviral agents. During the course of detailed studies involving the investigation of the replication of the infected by papilloma virus cells and the effect of various antiviral agent on that process, we have developed a novel method of growing cells in a monolayer cell culture system which allows for conducting the said novel antiviral tests.

A detailed embodiment of this invention involving cells RK-13 and Sf1Ep and CRPV as the studied virus is herein disclosed. However it is understood that the preferred embodiment is merely illustrative of the invention which may be embodied in various forms and applications accordingly, specific functional details disclosed herein are not to be interpreted as limiting, especially the type of virus, but merely as a support for the invention as claimed and as appropriate representation for teaching one skilled in art to variously employ the present invention in any appropriate embodiment.

An In Vitro Model System for Studying the Initial Stages of Cottontail Rabbit Papillomavirus CRPV Infection We describe here an in vitro system in which early events in CRPV infection can be studied. This model may be particularly useful in the analysis of additional monoclonal antibodies or other agents which may interfere with viral binding and/or penetration. The system can be used to examine the effectiveness of antiviral agents which act early in the infection process.

Studies with CRPV have been limited due to the lack of an adequate cell culture system. The purpose of the current study was to establish the susceptibility of a cottontail rabbit cell line (Sf1Ep) to infection with CRPV. Our question was whether infection of these cells would result in the production of CRPV-specific RNA and would be inhibitable by virus-neutralizing antibodies.

Previously described in vitro systems for studying CRPV have been based on cell lines derived from CRPV-associated carcinomas (Georges, et al., 1984, J. Virol., 51:530–538; Georges, et al., 1985, J. Virol., 55:246–250; Seto, et al., 1991, J. Invest. Dermatol., 97:327–333 ), on the transfection or exposure of murine cell lines to virus preparations (Watts, et al., 1983, Virology, 125:127–138), or on the infection/transfection of rabbit keratinocytes (Taichman, et al., 1984, J. Invest. Dermatol., 83:2s–6s; Meyers and Wettstein, 1991, Virology, 181:637–646). Among these, only studies utilizing carcinoma cell lines or transformed 3T3s have been analyzed at the transcriptional level. Both rabbit carcinoma and murine cell lines may be inadequate for use in studies involving virus penetration mechanisms. This is due to the species-specificity inherent in papillomavirus infections and to the potential loss of cell surface receptor expression on carcinoma cells. Primary cottontail (*Sylviganus floridanus*) rabbit keratinocytes are the best target cells for such studies because they are the natural host cell. Cottontail skin, in contrast to skin from domestic (*Oryctolagus cuniculus*) rabbits, is permissive for CRPV replication (reviewed by Kreider and Bartlett, 1981, Adv. Cancer Res., 35:81–110). Because of the difficulty in obtaining cottontails and culturing primary rabbit keratinocytes (Breidahl, et al., 1990, Irununol. Cell Biol., 68:119–126), we chose to examine the response of a cottontail epidermal cell line (Sf1Ep) to infection with CRPV.

We demonstrated that infection of Sf1Ep cells with CRPV virion resulted in the dose-dependent production of two major viral transcripts. Infection of these cells did not result in transformation and vira nucleic acids were lost from infected culture upon extended passage. Previously described neutralizing monoclonal antibodies to CRPV (Christensen and Kreider, 1991, Virus Res., 21:169–179), reduced both CRPV penetration and transcription.

At least two, but as many as five virus-specific RNA transcripts (1.25, 2.0, 2.5, 3.0 and 3.5 Kb) were detectable subsequent to in vitro CRPV infection while no viral RNA was found in mock-infected cultures (FIG. 1). Although CRPV transcripts were detectable as early as 17 hours post-infection, vira RNA was maximal between 2–6 days. Transcripts were diminished, beginning seven days post-infection, but were still detectable after 7 passages (21 days) post-infection. Two transcripts, 1.25 and 2.0 Kb, were the most abundant in infected cells. These were also the most abundant in domestic rabbit and cottontail papillomavirus lesions and correspond in size to transcripts from the E7 and E6 ORFs respectively. In both the domestic and cottontail lesions, these transcripts were present in nearly a 1:1 ratio. In in vitro infected cells the 2.0 Kb transcript was approximately 2–4 fold less abundant than the 1.25 Kb transcript (FIG. 1 and data not shown).

Figure 2:
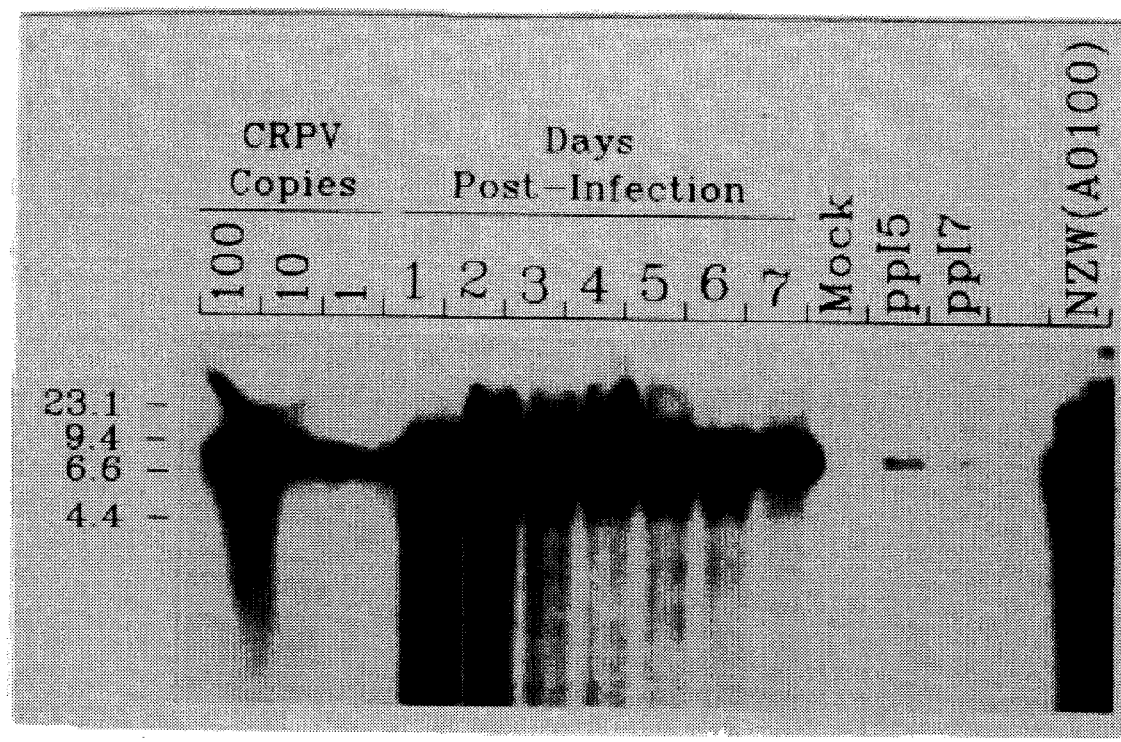
FIG. 2. Detection of CRPV DNA within infected Sf1Ep cultures. Each sample o represents 5 micrograms of total cellular DNA from cultures depicted in FIG. 1. All samples were digested with SalI. Full-length CRPV isolated from pLA2-CRPV was used to reconstruct 1, 10, and 100 copies per diploid genome equivalent (6.55, 65.5, 655 pg respectively). NZW (A0100) and mock represent DNA isolated from a New Zealand White (domestic) rabbit papilloma, and mock-infected cultures, respectively.

Restriction digests of CRPV DNA, isolated from infected cultures, with a single cutting enzyme SalI indicated that CRPV was present at between 50 and 100 episomal copies per cell DNA equivalent (FIG. 2). Unlike the RNA transcripts, viral DNA content did not increase with time, and pronounced decreases were seen with passages of infected cultures.

Figure 3:
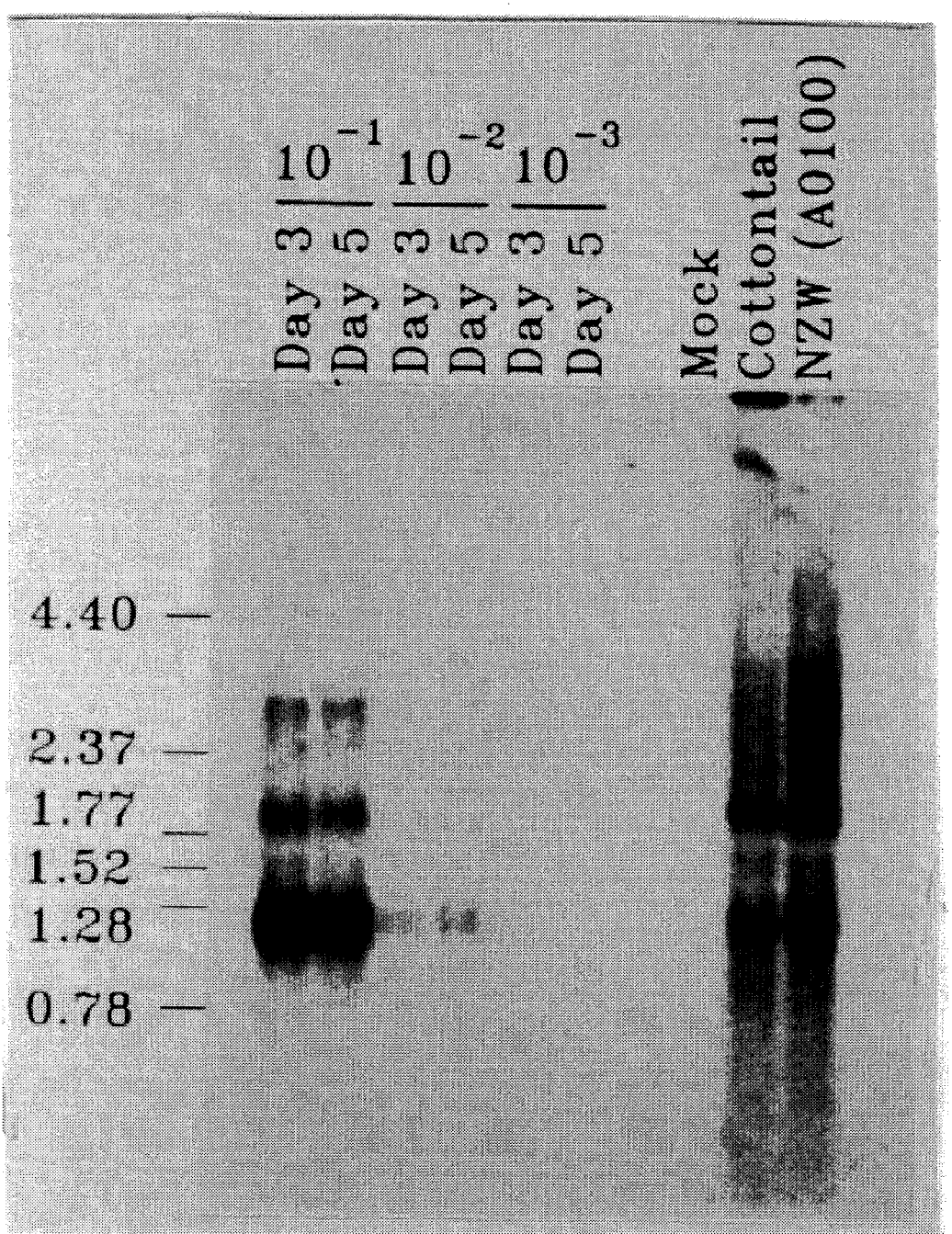
FIG. 3. Northern hybridization of total cellular RNA (10 µg) from Sf1Ep cultures infected with ten fold dilutions of CRPV. Cultures received 200 µl, 20 µl or 2 µl of CRPV stock in 2 ml total volume of media ($10^{-1}$, $10^{-2}$, or $10^{-3}$ respectively) Cottontail and NZW (A0100) represent RNA isolated from a CRPV-infected cottontail rabbit earskin papilloma cyst and New Zealand White (domestic) rabbit papilloma, respectively. Mock indicates RNA isolated from mock infected Sf1Ep cells. Marker positions indicate the migration of RNA standard ladders.
Figure 4:
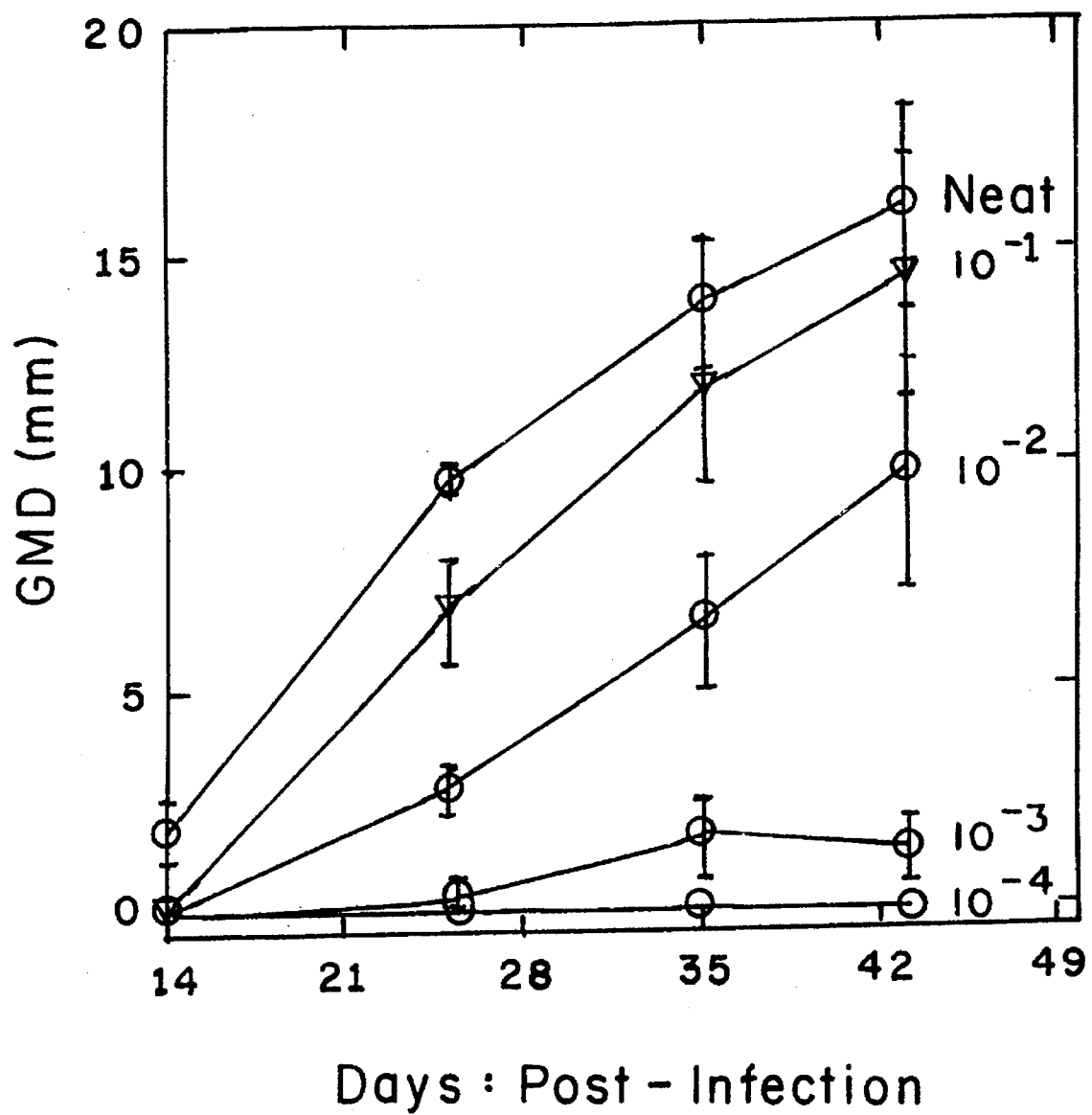
FIG. 4. Rabbit papilloma growth resulting from infection with serial dilutions of CRPV stock. Measurements are expressed as the geometric mean diameter of the lesion. Papillomas were generated with 50 µl of 10-fold serial dilutions of CRPV as in Materials and Methods.

To determine if the amount of vital RNA produced was a reflection of the CRPV copy number within infected cells, we examined the effect of using ten fold serial dilutions of viral stock in the in vitro infection of Sf1Ep cells. CRPV viral RNA was most abundant in cultures infected with a $10^{-1}$ dilution (200 μl) of viral stock. A dilution of $10^{-2}$ produced detectable amounts of RNA while a dilution of $10^{-3}$ did not produce vital RNA by 5 days post-infection (FIG. 3). This coincided with the amount of CRPV DNA within these cultures although cultures receiving a $10^{-3}$ dilution contained detectable, but low amounts of DNA (data not shown). These results correlated with the efficiency at which dilutions of the same viral preparation induced lesions in vivo. Lesions induced with a $10^{-1}$ viral dilution appeared earlier than lesions induced with a $10^{-2}$ dilution while those induced with a $10^{-3}$ dilution appeared much later (FIG. 4).

Figure 5:
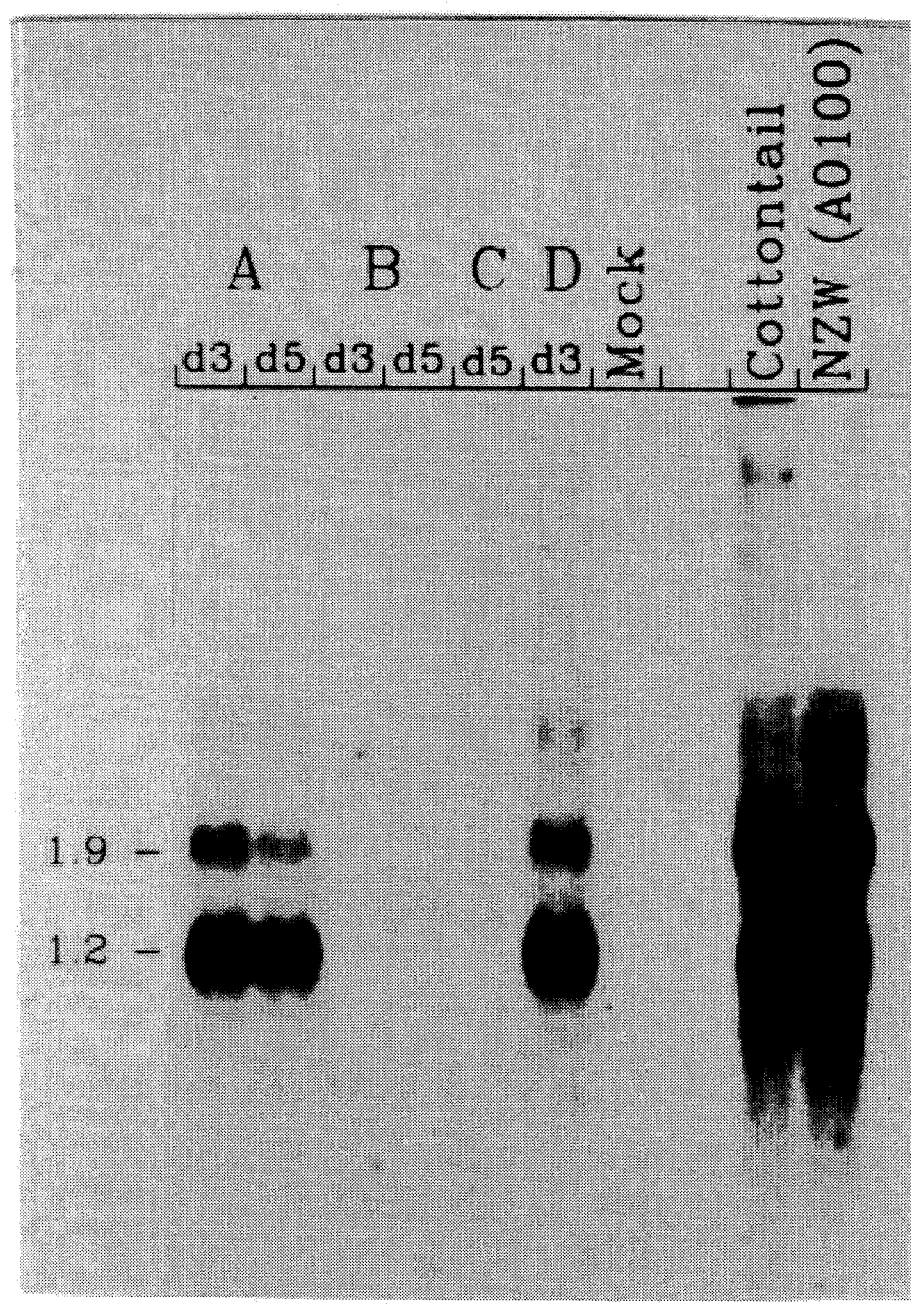
FIG. 5. Northern analysis of cellular RNA (10 µg) isolated from Sf1Ep cultures infected with CRPV preincubated 1 hour with: lane A) media only, lane B) CRPV-neutralizing monoclonal Ab (CRPV4B) 1:10 final dilution, lane C) CRPV-neutralizing monoclonal Ab (CRPV4B) 1:100 final dilution, or lane D) HPV-11 neutralizing monoclonal Ab (H11.B2) 1:10 final dilution. Mock indicates uninfected Sf1Ep cells. Cultures were harvested either 3 days or 5 days after infection. Cottontail and NZW (A0100) represent RNA isolated from a CRPV-infected cottontail rabbit earskin papilloma cyst and New Zealand White (domestic) rabbit papilloma respectively.
Figure 6:
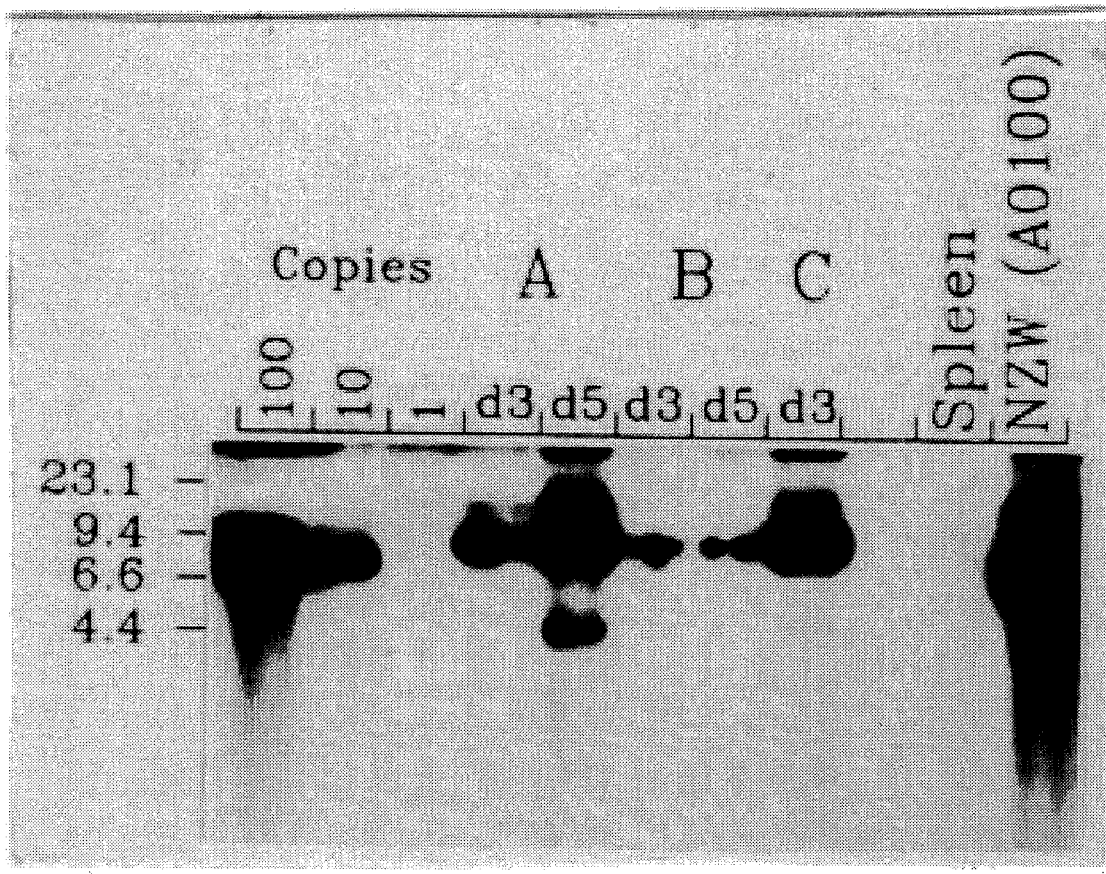
FIG. 6. Southern analysis of SalI-cleaved cellular DNA (5 gg) from Sf1Ep cultures infected with CRPV preincubated with the monoclonal Abs listed in FIG. 5. Lane A) CRPV preincubated with media only; lane B) CRPV preincubated with CRPV4B 1:10 final dilution; lane C) CRPV preincubated with H11.B2 1:10 final dilution. NZW (A0100) indicates CRPV DNA isolated from a New Zealand White (domestic) rabbit papilloma. Spleen represents spleen DNA isolated from a NZW rabbit.

Prior incubation of CRPV with a neutralizing monoclonal antibody to CRPV (CRPV4B) inhibited viral RNA production in Sf1Ep cells, while another isotype-matched control antibody (H 11.B2), neutralizing for HPV-11, did not (FIG. 5). The initial dilution of the antibody stocks used (1:10) had been previously shown to be neutralizing for HPV-11 or CRPV in vivo. Whereas H11.B2 had no inhibitory activity at this level in our system, CRPV4B was still inhibitory even at a 1:100 dilution. This inhibitory activity did not change with a prolonged culture period of five days. Southern blots of these neutralized cultures show that in most cases persisting CRPV DNA was greatly reduced relative to control and H11.B2 treated cultures (FIG. 6).

The objective of the present study was to establish an in vitro infection system for CRPV in which a marker, in this case RNA production, was dependent upon infection with intact virion. We selected the Sf1Ep cell line for this system for two reasons: a) proper tissue; b) proper host. The source material for this cell line was derived from the epidermis of the natural host, the cottontail rabbit. In addition, this cell line, unlike others, was not previously transformed and contained replicating as well as senescent cell populations.

Other investigators have reported the use of this cell line in CRPV transfection studies (Meyers and Wettstein, 1991, Virology, 181:637–646; Meyers, et al., 1992, J. Virol., 66:1655–1664). These analyses did not involve the use of virion nor was CRPV transcription within transfected cells described. The authors did report transformation-associated changes in transfected cells that represented cell enlargement with the presence of intracytoplasmic inclusions. We occasionally observed this phenomenon within our infected cultures held for at least 30 days without passage. The time course of CRPV RNA production in infected cells was comparable to that reported for abortive infection of bronchial epithelial cells by HPV-1 (Christian, et al., 1987, In: Cancer Cell 5, Cold Spring Harbor Laboratory, N.Y., pp 165–170). The time delay of approximately 24 hours before the accumulation of abundant viral RNA transcripts may be due to the time required for vital uncoating and/or viral DNA replication. The reason for the decline in viral RNA and DNA amounts upon passage is unclear. Previous studies with HPV-1 infections in vitro indicate that infected cells containing a high copy number of viral DNA, detached from the flask and were lost in passage (Reilly and Taichman, 1987, In: Cancer Cells 5. Cold Spring Harbor Laboratory, N.Y., pp 159–164). This may also occur here since infected flasks contained significantly more floating/non-viable cells than comparable confluent, uninfected flasks. Likewise, CRPV viral DNA may be underreplicated with respect to the cell genome as was also described for HPV-1.

The most abundant viral transcripts corresponded in size to those of the E6 and E7 ORFs of CRPV. It is interesting, given the abundance of these transcripts, and despite the reported roles of the E6 and E7 ORFs in transformation, that our infected cells were not immortalized and, thus far, have been unable to form tumors in nude mice (unpublished observations). It is also interesting that the greater relative abundance of the 1.25 Kb transcript, consistently seen in infected Sf1Ep cells, has been associated with transcripts from malignant CRPV lesions. In contrast, the levels of the 1.25 and 2.0 Kb transcripts were approximately equal in our benign papilloma controls.

Infection here, using the production of CRPV transcripts as an indicator, was inhibited by monoclonal antibodies that neutralize CRPV infections in vivo. The reduced amounts of DNA present within infected cultures indicate that neutralization most likely occurred by inhibition of vital binding/ penetration. The specificity of this event was demonstrated by the fact that isotype-matched monoclonal antibodies which neutralized HPV-11 had minimal effect on CRPV.

Materials and Methods Cell Lines, Antibodies and Virus

Sf1Ep cells (NBL-11) were obtained through the American Type Culture Collection, Rockville, Md. Cell cultures were maintained in Basal Medium Eagle (GIBCO, Grand Island, N.Y.) supplemented (as complete media) with 1.5 g/l sodium bicarbonate, 10 mM HEPES, 2 mM L-glutamine, 100 μM non-essential amino acids (Sigma, St. Louis, Mo.), 1 mM sodium pyruvate (GIBCO, Grand Island, N.Y.), 100 U/100 μg/ml penicillin/streptomycin, and 10% fetal bovine serum. Sf1Ep cells were utilized at passages 80–90. Monoclonal antibodies H11.B2 and CRPV4B were used as culture supernatants containing Clonetic's media (Clonetics Corp., San Diego, Calif.) and 5% keratinocyte conditioned media. These antibodies neutralize HPV-11 and CRPV respectively in vivo (Christensen, et al., 1990, J. Virol., 64:5678–5681; Christensen and Kreider, 1991, Virus Res., 21:169–179). CRPV was obtained as a crude extract from CRPV-infected cottontail earskin implanted subcutaneously in athymic nude mice. CRPV-producing earskin cysts were homogenized in an extraction buffer (1M NaCl, 20 mM Tris pH 7.4, 2 μg/ml PMSF) on ice in a Virtis homogenizer at 30 K RPM for 5 minutes. The homogenates were centrifuged at 10,000× g for 20 minutes at 4° C. The resulting supernatants were stored at −70° C. Prior to use, viral stocks were quickly thawed, sonicated for 1 minute and centrifuged for 5 seconds.

Nucleic acid extraction

For total RNA, cell monolayers were rinsed with Hank's balanced salt solution, without calcium and magnesium (HBSS), and lysed with 4M guanidinium isothiocyanate, 0.1 mM DTT, 0.5% N-lauroylsarcosine, 20 mM sodium acetate pH 5.2. Lysates were layered over a 5.7M CsCl cushion and centrifuged in a SW55Ti rotor at 35,000 RPM for 20 hr at 18° C. RNA pellets were resuspended in 10 mM Tris-Cl, 5 mM EDTA, 1% SDS followed by subsequent precipitation with 0.3M sodium acetate and absolute ethanol. DNA was extracted from TE-dialyzed guanidinium/CsCl supernatants by proteinase K digestion (100 μg/ml) followed by sodium acetate/absolute ethanol precipitation.

Northern blotting and hybridization

Ten micrograms total cellular RNA was size fractionated by electrophoresis through a 1.4% agarose/8% formaldehyde gel and transferred to Zetaprobe nylon membranes (BioRad, Rockville Center, N.Y.) with 10× SSC (1.5M sodium chloride, 0.15M sodium citrate) by capillary action. CRPV genomic sequences were isolated from a pLA2-CRPV construct (Mellon, et al., 1981, Cell, 27:279–288) (obtained from F. Wettstein) by SalI digestion and labelled to a specific activity of at least $5 \times 10^8$ CPM/μg by random hexamer $^{32}$P-dATP labelling utilizing the Multiprime labelling system (Amersham, Arlington Heights, Ill.). Filters were prehybridized for 30–60 minutes and then hybridized for 24 hrs at 65° C. utilizing a buffer of 7% SDS, 0.5M $NaH_2PO_4$ pH 7.2, 1 mM EDTA. Filters were then washed at 65° C. 2x with 5% SDS, 40 mM NaH2PO4 pH 7.2, 1 mM EDTA followed by two additional washes utilizing the same buffer with 1% SDS.

Southern blotting and hybridization

Five micrograms of total cellular DNA was digested with SalI (CRPV single cutter) using manufacturer's protocol. Digested DNA was sized fractionated on a 0.8% agarose gel and then transferred to Zetaprobe nylon membranes with 0.4N NaOH after depurination with 0.25N HCl. Prehybridization and hybridization conditions were as stated above for northern blots.

In vitro monolayer infection system

Two days prior to infection, $5 \times 10^5$ Sf1Ep cells were seeded into T75 flasks with Eagle's complete media. On the day of infection, the cultures were typically 50% confluent. Flasks were rinsed once with HBSS and infected with 2 mls of a ten-fold dilution of CRPV in Eagle's complete media without serum. Infected flasks were incubated for 2 hours at 37° C./5 % $CO_2$ on a slowly rocking platform. After infection, residual inoculum was removed and the flasks rinsed three times with HBSS. Each flask was then fed 10 mls of Eagle's complete media with 10% FBS.

In vivo CRPV infection

Two New Zealand White rabbits (Hazelton Research Labs, Denver, Pa.) were infected with 10-fold serial dilutions of the CRPV stock prepared as above. Lesions were initiated by the application of 50 μl of neat virus or virus diluted with PBS on abraded areas of the dorsal skin. Two sites per dilution were inoculated per rabbit Tumor measurements were made in three dimensions and the geometric mean diameter (GMD) was calculated per tumor.

Antibody-mediated neutralization

Murine monoclonal antibodies neutralizing for CRPV (CRPV4B) or HPV-11 (H11.B2) were generated and analyzed as previously published (Christensen, et al., 1990; Christensen and Kreider, 1991). Antibody dilutions were made in Eagle's complete media without serum. Prior to infection, 1 ml of 5-fold diluted CRPV stock was incubated with 1 ml of diluted antibody, or media alone, for 1 hr at 37° C. on a rocking platform. After incubation, the antibody-CRPV mixture was added to culture flasks as described above.

Development of the novel method of testing antiviral activity by employing known antiviral agents as the model substrate.

Two well define in other experimental systems agents PMEG (9-(2-phosphonylmethoxy) ethyl-guanine, E. De Clepcq, et al., 1986, Nature, 323:464–467) and HPMPC ((s)-1-(3-hydroxy-2-(phosphonylmethoxy)propyl)-cytosine, A. Merta et al., 1990, Antiviral. Res., 13:209–218) were used to test the effectiveness of this method.

PMEG AND HPMPC Treatments

This system uses the Sf1Ep (rabbit cottontail) cell line as an infection target. Recently the use of another rabbit cell line (RK-13) has been included. Both cell lines are cultured in Eagle's Basal Media (with Earls's Salts) containing L-glutamine, Pen/Strep, non-essential amino acids, HEPES, $NaHCO_3$ and fetal bovine serum (10% final volume). For each experiment $5 \times 10^5$ Sf1Ep cells (or $1 \times 10^6$ RK-13 cells) are plated in T75 flasks with the above medium. The cells are incubated for 48 hours and then infected for 2 hours with a standard dilution of CRPV viral stock (2 ml volume of virus in the above medium without FBS). After the infection, the cells are rinsed 2× with PBS and 9 mls of culture media (with FBS) are then added per flask. One milliliter of 10× drug (PMEG or HPMPC) solutions are added to the appropriate flasks. For PMEG, 100 μg, 10 μg and 1 μg/ml stocks were used to yield 10 μg/ml, 1 μg/ml, 1.0 μg/ml final concentrations. HPMPC dosages started 100 fold higher than the PMEG due to the reduced toxicity of this compound. Diluent for both drugs, as well as the drug free control consisted of sterile 0.9% saline solution. The infected cells were incubated for 4–6 days post-infection with the media (± drug) being changed every other day. Cell counts were performed daily or every other day by directly counting adherent cells using an ocular micrometer at a 100× total magnification. After 4–6 days the cells are harvested by lysis with guanidinium thiocyanate and the nucleic acids extracted by conventional methods as described.

Figure 7:
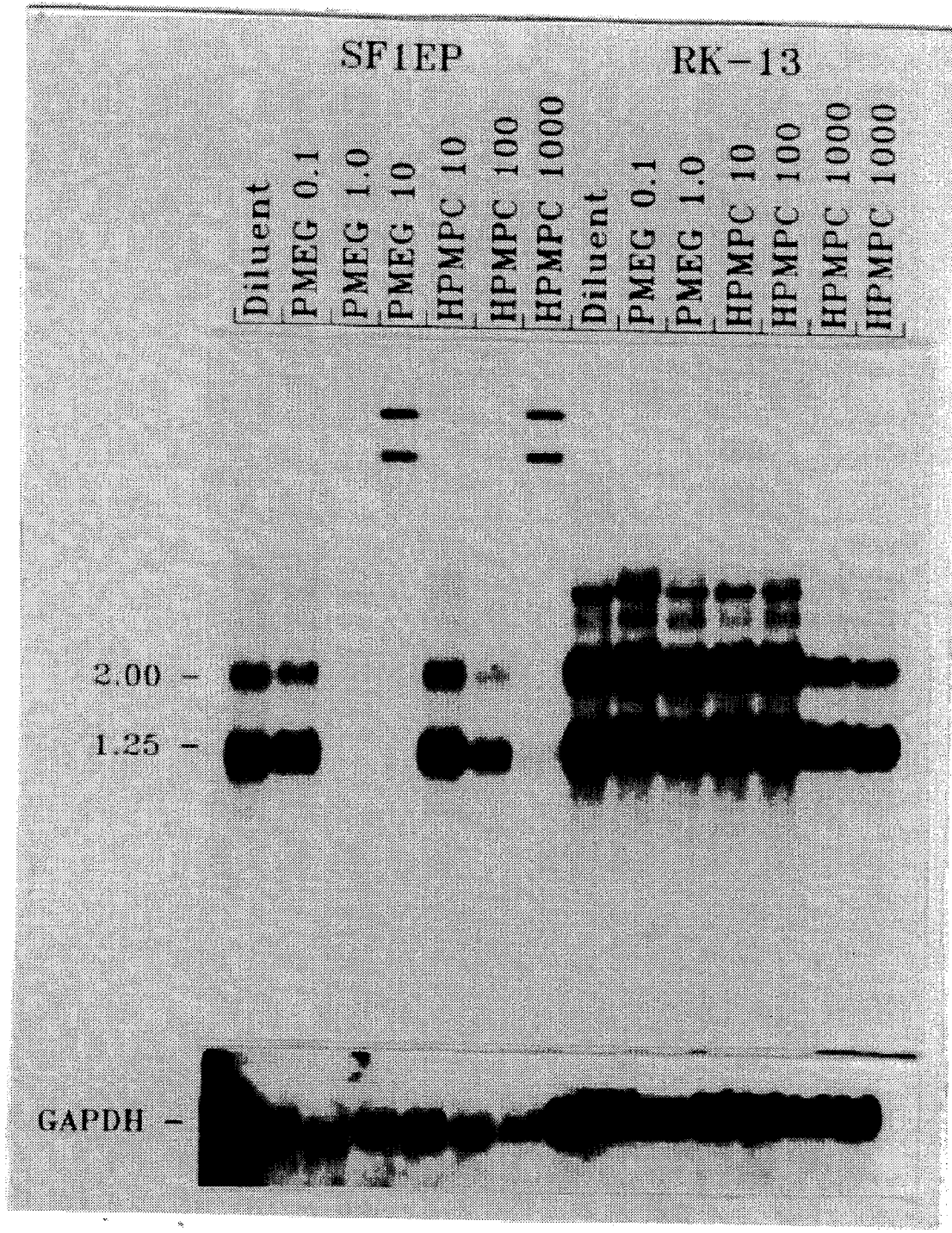
FIG. 7. Comparison of CRPV transcripts produced in CRPV-infected cultures treated with either PMEG or HPMPC.
Figure 8A:
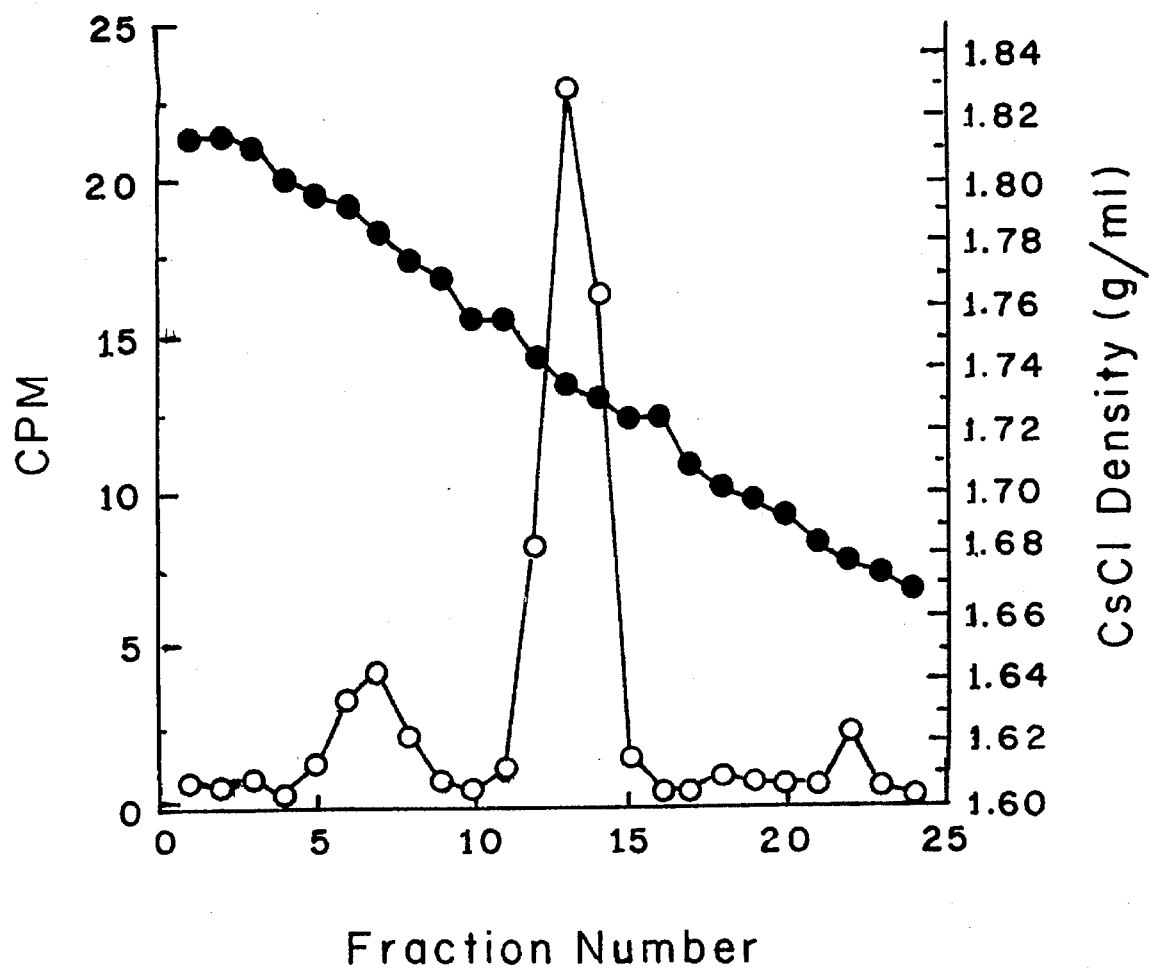
FIG. 8A Presents growth rates from CRPV-infected Sf1Ep cells treated with HPMPC.
Figure 8B:
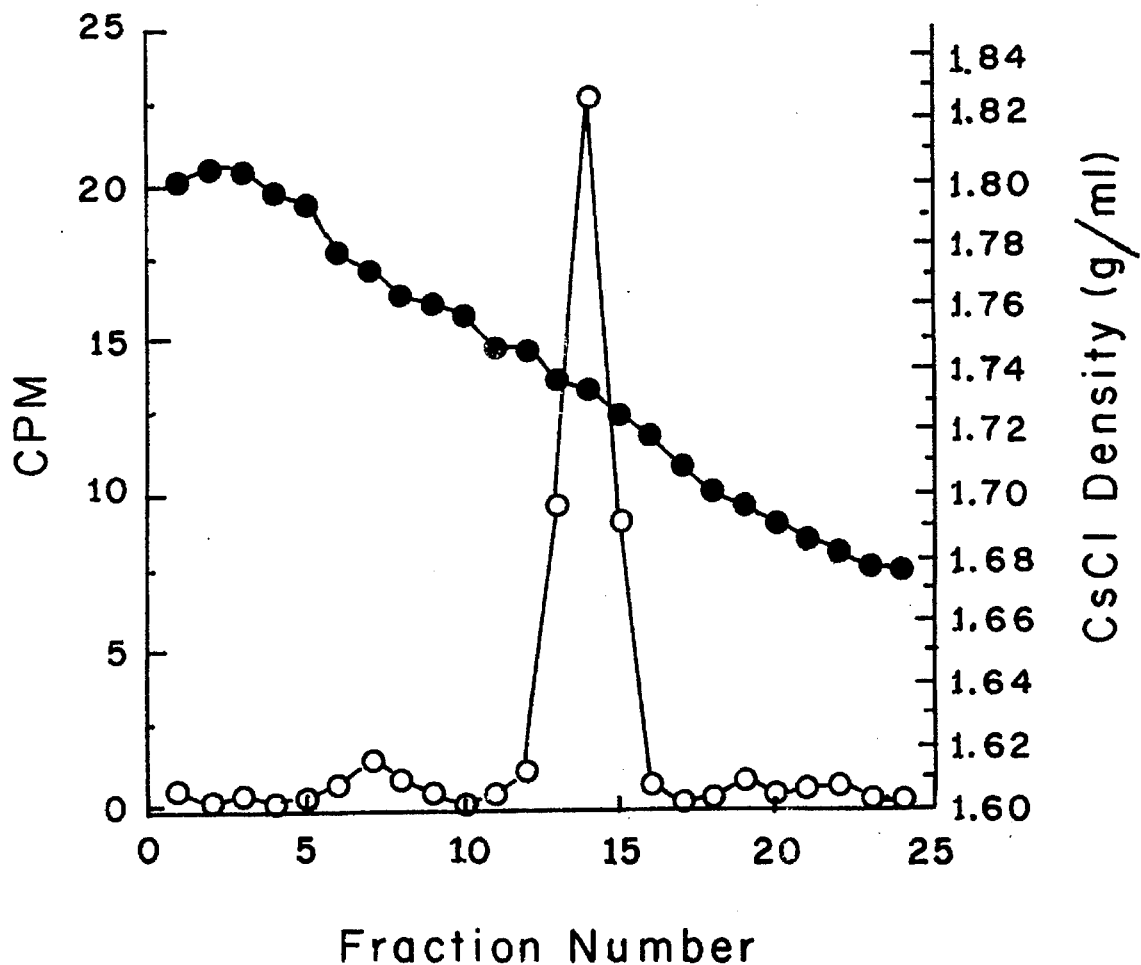
FIG. 8B Presents growth rates from CRPV-infected Sf1Ep cells treated with PMEG.
Figure 8C:
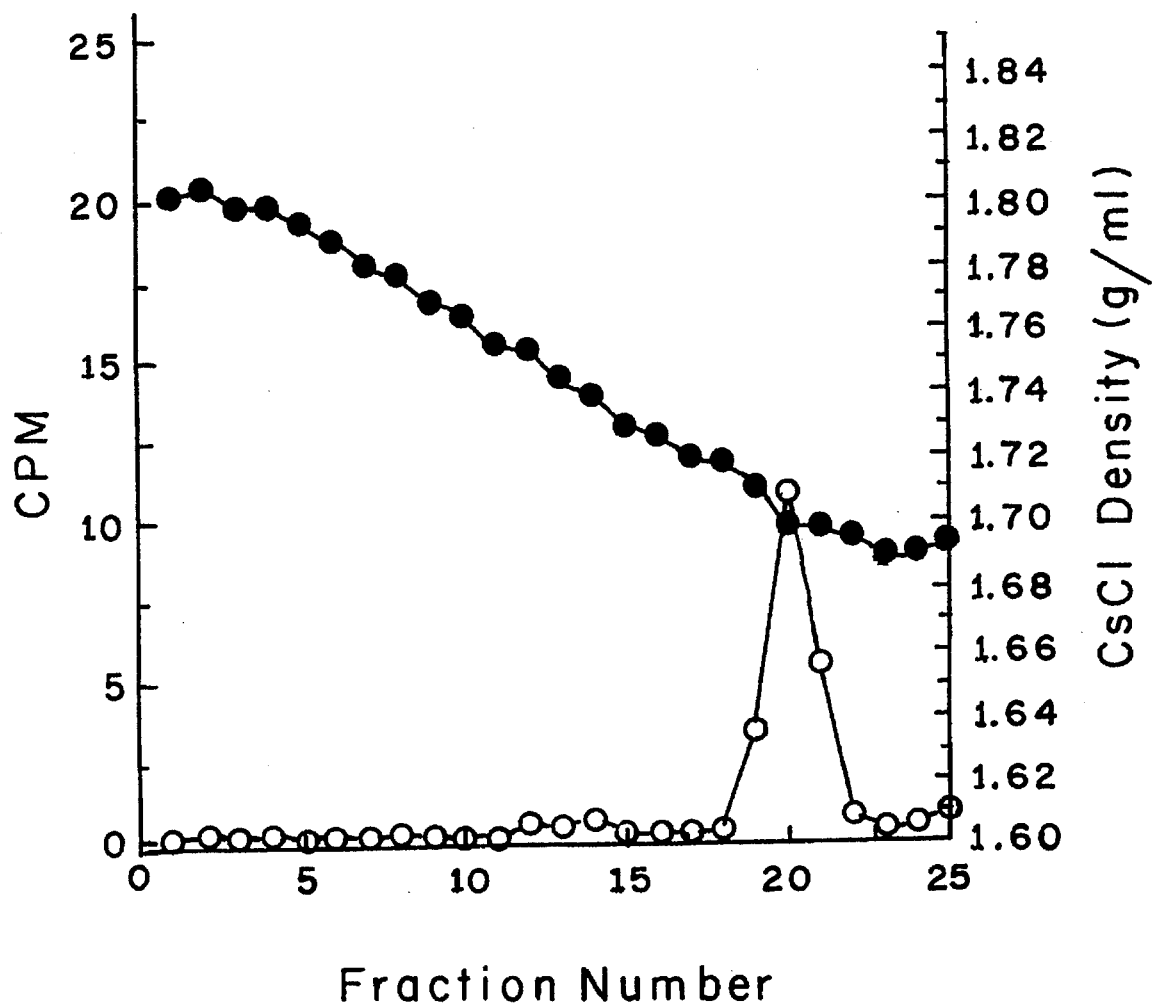
FIG. 8C Presents growth rates of the uninfected Sf1Ep cells treated with HPMPC.
Figure 8D:
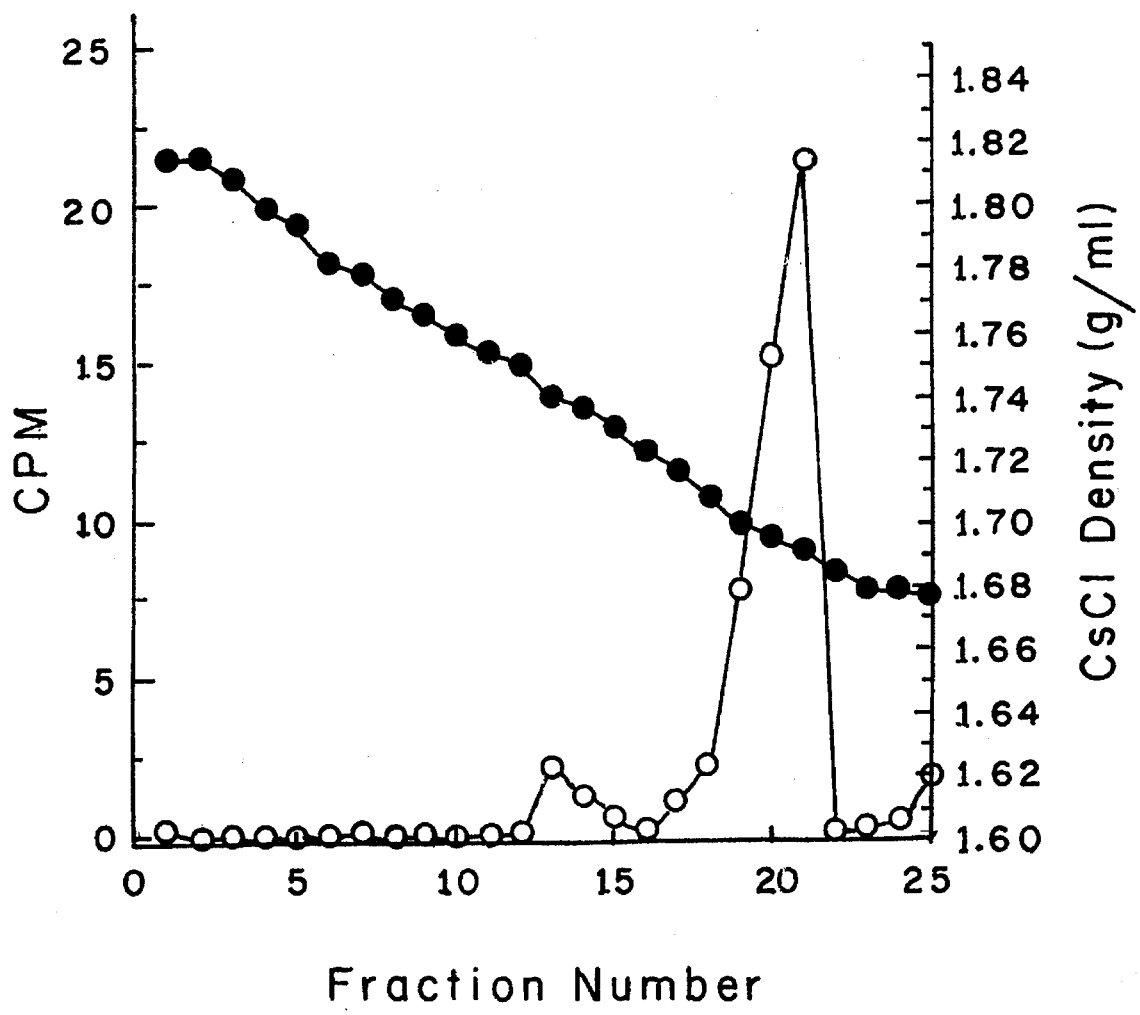
FIG. 8D Presents growth rates of the uninfected RK-13 cells treated with HPMPC.
Figure 9A:
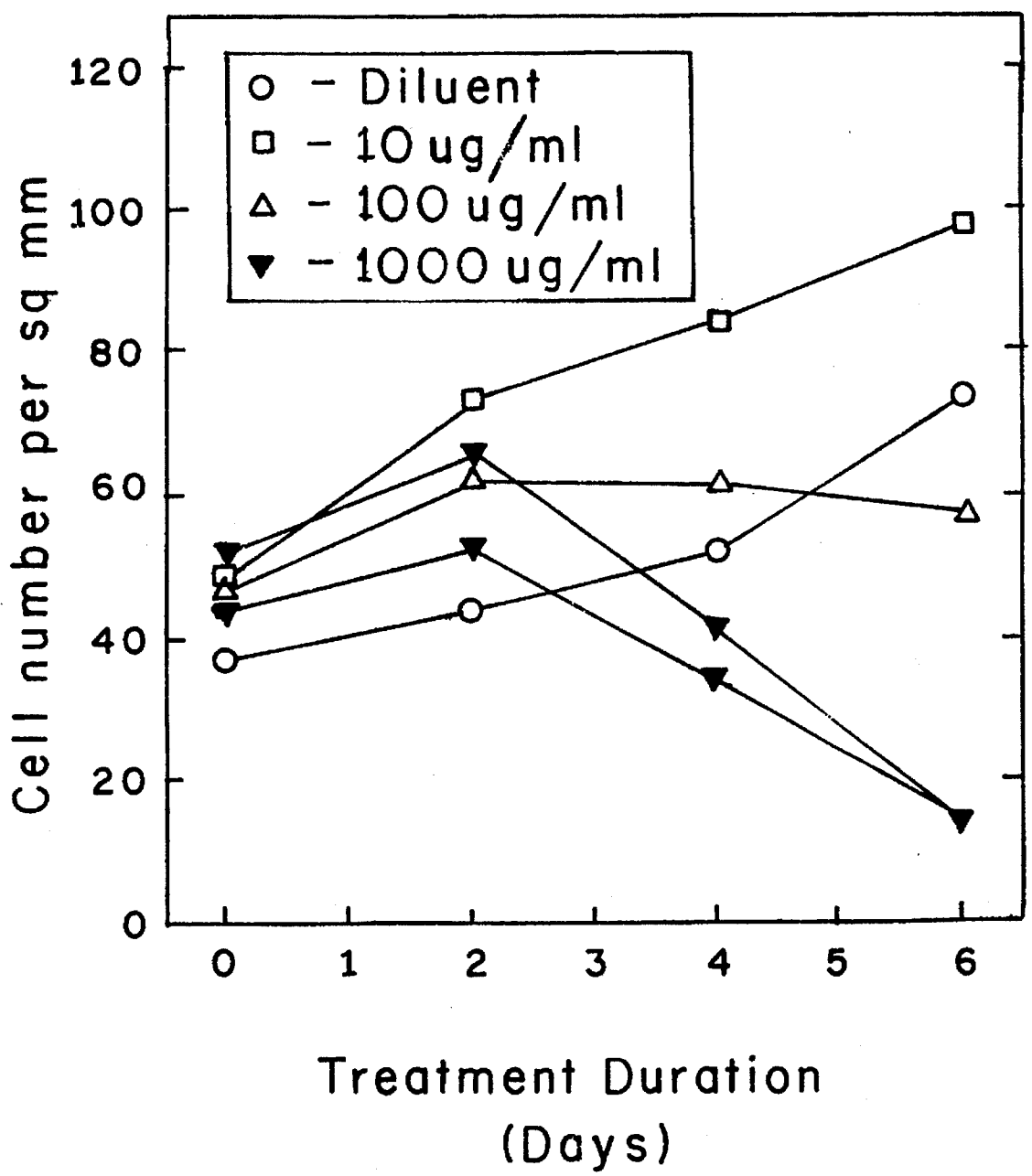
FIGS. 9A and B Present the level of BRdU-labeled (replicated) viral DNA in mock-treated CRPV-infected Sf1Ep cells at 90 hours post-infection.
Figure 9C:
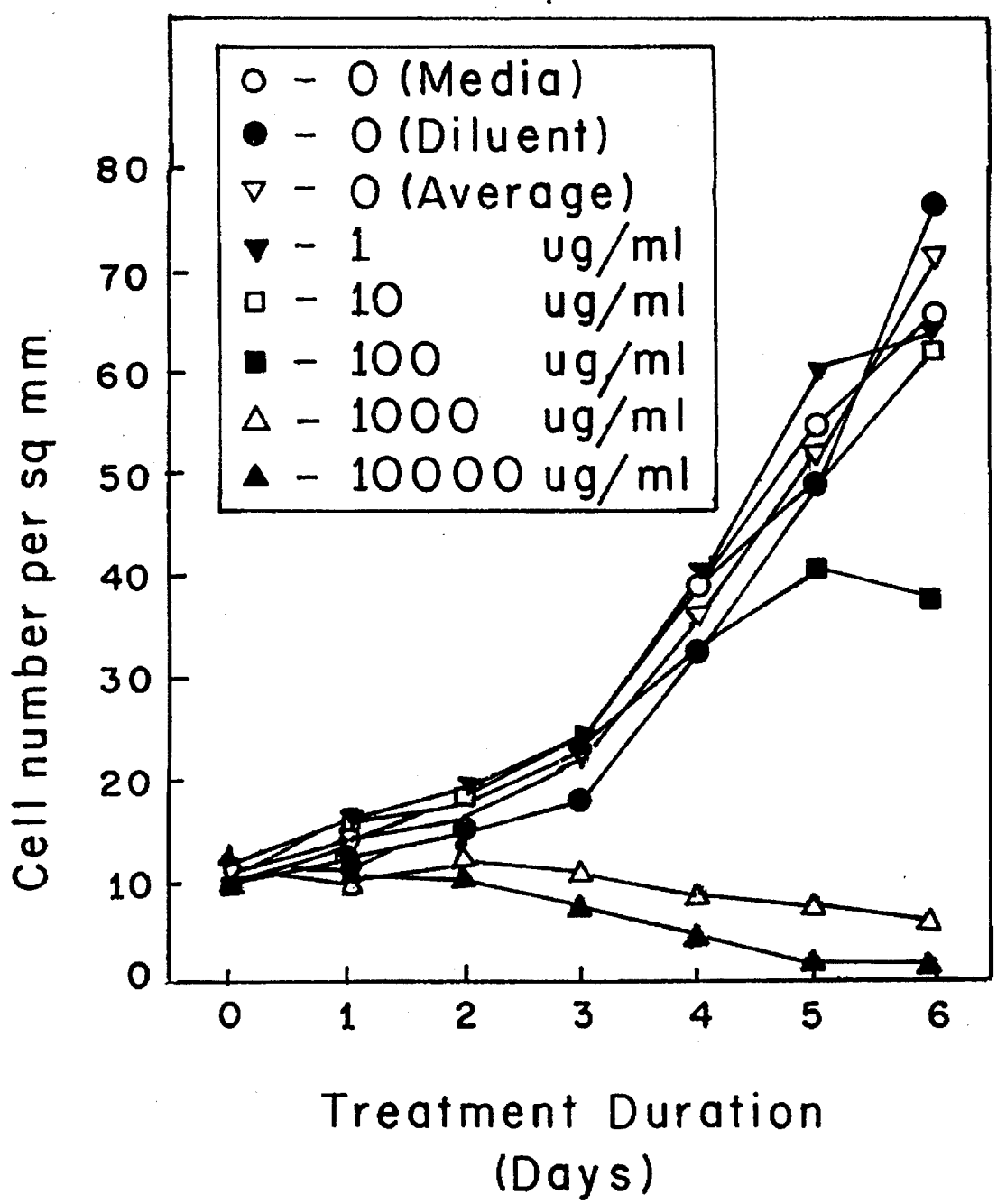
FIGS. 9C and D Present the level of BRdU-labeled (replicated) viral DNA in interferon-treated Sf1Ep cells 130 hours post- infection.
Figure 9D:
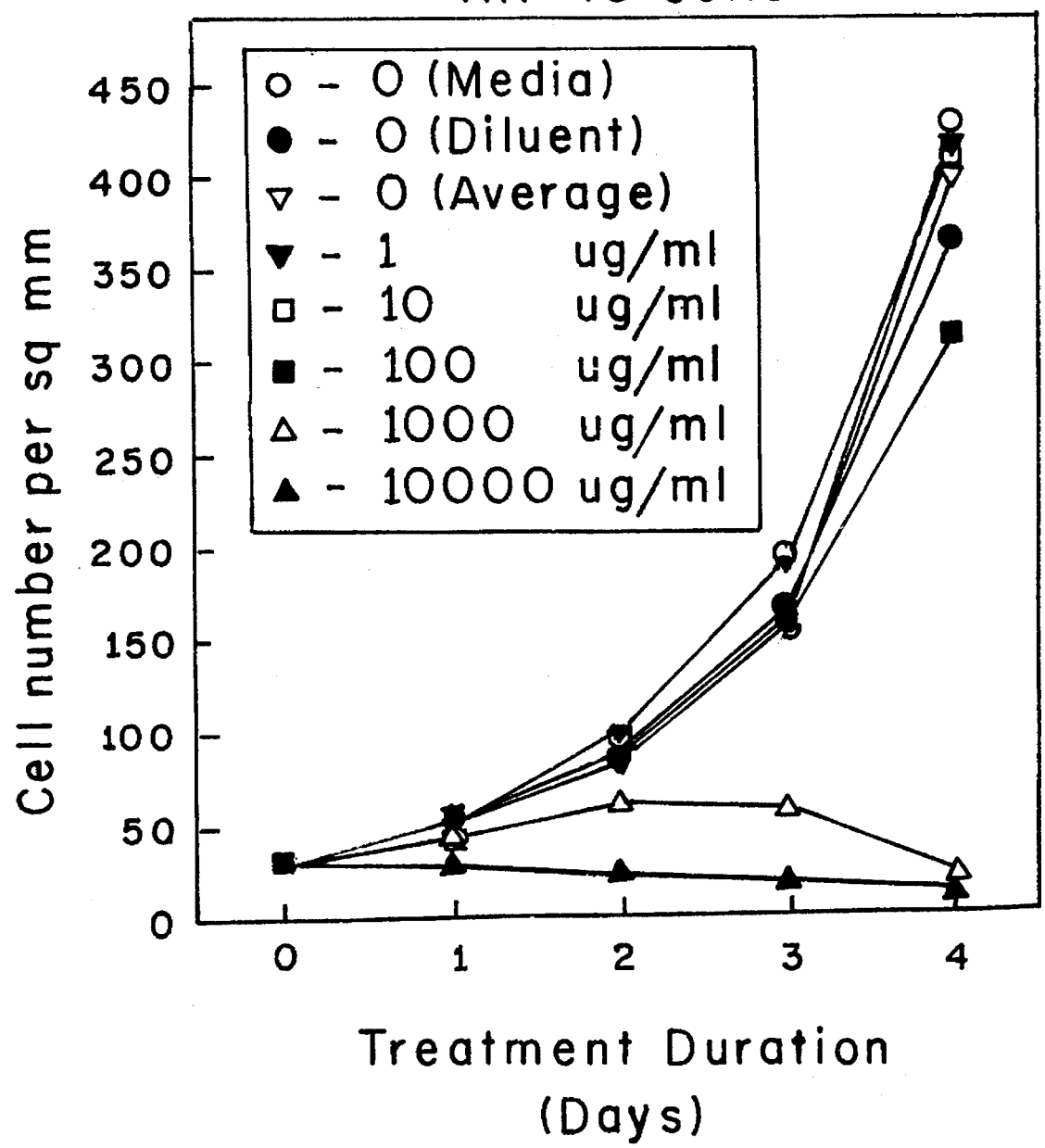

CRPV infected Sf1Ep or RK-13 cells were treated with PMEG (0.1–10 μg/ml) or HPMPC (10–1000 μg/ml) for 4–6 days. Effects on CRPV transcription (FIG. 7) and cell proliferation/viability were examined.

Treatment of CRPV-infected Sf1Ep cells with either drug resulted in a reduction of CRPV transcripts at doses found to be growth inhibitory or toxic (FIGS. 8A–D). In contrast, the effects of both drugs on CRPV transcription in infected RK-13 cells were less pronounced even though PMEG and HPMPC at doses of 1.0 μg/ml and 1000 μg/ml respectively were found to be toxic to uninfected cells.

The nature of the inhibitory effect of both drugs is unknown, however generalized suppression of RNA transcription is probably not responsible due to the continued expression of GAPDH in the highest treatment groups. We have previously demonstrated that RNA transcript abundance is dependent upon CRPV DNA copy number. Whether drug treatment results in a reduction in CRPV copy number or whether cells containing a high copy number are more sensitive to drug toxicity is unclear.

Effect of Rabbit Fibroblast Interferon (nRaIFN) on CRPV DNA Synthesis In Vitro

We used our CRPV/Sf1Ep infection system to examine the ability of nRaIFN to inhibit CRPV DNA synthesis. CRPV-infected Sf1Ep cells were cultured for up to 6 days in the presence of 1000 U/ml nRaIFN (Lee Biomolecular rabbit fibroblast IFN). At 2, 4, and 6 days post infection, treated and untreated cultures were pulsed with BRdU for 36 hours. The DNA from pulsed cultures was then resolved on a CsCl gradient to separated replicated (BRdU-substituted) and unreplicated DNA. By 90 hours after infection, approximately 93% of the CRPV DNA in IFN treated cells had replicated at least once as compared to 89% in CRPV-infected, IFN-untreated cells. No difference was seen at 130 hours either with approximately 7% of the CRPV DNA being replicated in the IFN treated flask vs. approximately 5% in the untreated flask. No CRPV DNA replication occurred in either group at 6 days post-infection. The drop in CRPV DNA replication between the two time points is most likely due to suppression of cellular DNA synthesis as a result of culture confluency (FIGS. 9A–D).

We believe that these data indicate that this system will be useful to study selected antivirals for their effects on early stages of papillomavirus infections, especially vital DNA synthesis and expression.

The method provides a mean to conduct a preliminary studies of the potential drugs. We also believe that this stage of the infection is critical to viral persistence in the papillomavirus-infected cell and therefore a more relevant target for antivirals than is the formation of complete virions in differentiated cells. This later phase occurs sparsely in most human lesions and not at all in "inapparent" or latent infections, which are the likely source of lesion recurrences post-treatment.

The invention described herein provides a novel model for studying antiviral effectiveness of various agents. We believe that this in vitro system is sufficiently consistent or precise to form a basis for a testing method.

The present invention offers a method which precisely measures antiviral activity without the interferences of the regional variability of organ cultures.

Thus, while I have illustrated and described the preferred embodiment of my invention, it is to be understood that this invention is capable of variation and modification, and I, therefore, do not wish or intend to be limited to the precise terms set forth, but desire and intend to avail myself of such changes and alterations which may be made for adapting the invention of the present invention to various usages and conditions. Accordingly, such changes and alterations are properly intended to be within the full range of equivalents and, therefore, within the purview of the following claims. The terms and expressions which have been employed in the foregoing specification are used therein as terms of description and not of limitation, and thus there is no intention in the use of such terms and expressions of excluding equivalents of features shown and described or portions thereof, it being recognized that the scope of the invention is defined and limited only by the claims which follow.

Thus is described my invention and the manner and process of making and using it in such full, clear, concise, and exact terms so as to enable any person skilled in the art to which it pertains, or with which it is most nearly connected, to make and use the same.

What is claimed is:

1. An in vitro system for testing antiviral activity of agents wherein said system is free of interferences caused by regional variability of organ cultures and wherein the antiviral agent interferes with early and maintenance stages of papillomavirus infection, said system comprising the steps of:

growing rabbit epithelial cells susceptible to infection by Cottontail Rabbit Papillomavirus in a monolayer system;

infecting the rabbit epithelia cells with the Cottontail Rabbit Papillomavirus;

introducing an antiviral agent to a growing culture of infected rabbit epitheial cells; and measuring expression of nucleic acids in the rabbit epithelial cells growing in the presence or absence of the antiviral agent as a measure of effectiveness of the antiviral agent to interfere with growth of the Cottontail Rabbit Papilloma Virus.

2. The method of claim 1, wherein said rabbit epithelial cells grown, and infected, in the monolayer system do not complete cytodifferentiation post-infection.

3. The method of claim 1, wherein the testing is performed within 2 to 3 days post infection with the Cottontail Rabbit Papillomavirus depending on the amount of virion used.

4. The method of claim 1, wherein said rabbit epithelial cells are Sf1Ep cells.

5. The method of claim 1, wherein said rabbit epithelial cells are RK-13 cells.

* * * * *